United States Patent [19]

Carroll et al.

[11] Patent Number: 5,759,945

[45] Date of Patent: Jun. 2, 1998

[54] PREPARATION OF TITANIUM-CONTAINING CATALYSTS USING TITANOSILOXANE POLYMERS

[75] Inventors: Kevin M. Carroll, Havertown; Yuan-Zhang Han; Edrick Morales, both of West Chester, all of Pa.

[73] Assignee: Arco Chemical Technology, L.P., Greenville, Del.

[21] Appl. No.: 824,598

[22] Filed: Mar. 26, 1997

[51] Int. Cl.⁶ .................................................. B01J 21/08
[52] U.S. Cl. ...................................................... 502/242
[58] Field of Search ............................................ 502/242

[56] References Cited

U.S. PATENT DOCUMENTS

| Re. 32,107 | 4/1986 | January | 501/12 |
|---|---|---|---|
| 3,166,542 | 1/1965 | Orzechowski | 260/93.7 |
| 3,220,959 | 11/1965 | Orzechowski | 252/441 |
| 3,274,120 | 9/1966 | Aftandillan | 252/432 |
| 3,873,578 | 3/1975 | Bell et al. | 260/348.5 |
| 3,923,843 | 12/1975 | Wulff | 260/348.5 |
| 4,367,342 | 1/1983 | Wulff et al. | 549/529 |
| 4,876,372 | 10/1989 | Nakanishi et al. | 549/529 |
| 4,968,842 | 11/1990 | Palovan et al. | 564/253 |
| 5,011,953 | 4/1991 | Nakanishi et al. | 549/529 |

FOREIGN PATENT DOCUMENTS

| 0345856 | 12/1989 | European Pat. Off. |
|---|---|---|
| 0731764 | 10/1996 | European Pat. Off. |
| 3205648 | 8/1983 | Germany |
| 1332527 | 10/1973 | United Kingdom |
| 9423834 | 10/1994 | WIPO |
| 9609117 | 3/1996 | WIPO |

OTHER PUBLICATIONS

Hutter, R. et al. 'Titania Silica Aerogels with Superior Catalytic Performance in Olefin Epoxidation Compared to Large Pore Ti Molecular Sieves.' Top. Cat. 1996. 3(3,4), pp. 421–436.

Fraile et al. *J. Chem. Soc., Chem. Common* 539–540 (1995).

Kooyman et al. *Proceedings of the 9th International Zeolite Conf.* Montreal 1992, 505–512.

Jorda et al. *J. Chem. Soc., Chem. Commun.* 1775–1776 (1995).

Castillo et al., *J. Catalysis* 161, 524–529 (1996).

*Primary Examiner*—Bernard Dentz
*Assistant Examiner*—Garth M. Dahlen
*Attorney, Agent, or Firm*—Stephen D. Harper

[57] ABSTRACT

A heterogeneous catalyst suitable for use in an olefin epoxidation reaction is obtained using a titanosiloxane polymer as a source of titanium. The titanosiloxane is combined with an inorganic siliceous solid such as silica or a siliceous sol gel to form a catalyst precursor composition. Calcination yields the active titanium-containing catalyst.

34 Claims, No Drawings

PREPARATION OF TITANIUM-CONTAINING CATALYSTS USING TITANOSILOXANE POLYMERS

FIELD OF THE INVENTION

This invention relates to heterogeneous titanium-containing catalysts prepared using titanosiloxane polymers as a source of titanium. The catalysts are obtained by combining the titanosiloxane polymer with an inorganic siliceous solid or siliceous sol gel and calcining. The materials thus produced are active catalysts for the selective epoxidation of olefins using organic hydroperoxides.

BACKGROUND OF THE INVENTION

Many different methods for the preparation of epoxides have been developed. One such method involves the epoxidation of an olefin in a liquid phase reaction using an organic hydroperoxide as the oxidizing agent and certain solubilized transition metal compounds as catalyst. The early work in this field concluded that optimum epoxidation rates and selectivity to epoxide generally are obtained using metallic catalysts which are soluble in an organic reaction medium. One example of a homogeneous metallic epoxidation catalyst is described in U.S. Pat. No. 3,873,578, wherein a soluble polyorganotitanosiloxane polymer is used to catalyze olefin epoxidation using an organic hydroperoxide.

A distinct disadvantage of an epoxidation process which utilizes a soluble metallic compound as catalyst is the difficulty associated with recovering the catalyst for reuse in subsequent runs. When the other components of an epoxidation reaction mixture (typically, epoxide, unreacted olefin, solvent, unreacted hydroperoxide, and the alcohol derived from the reacted hydroperoxide) are relatively volatile, these components may be separated from the soluble non-volatile catalyst by distillation and the catalyst recovered in the form of a bottoms stream. A problem associated with such a method, however, is that the bottoms stream may tend to accumulate certain heavy substances such as acids and polymers which may have a deleterious effect on epoxide selectivity or olefin conversion when the stream is reused. The catalyst may also have a tendency to precipitate from solution if the bottoms stream is overly concentrated; recycle of a relatively large bottoms stream may thus be required, which will detrimentally affect the productivity of the epoxidation process. It would therefore be highly desirable to develop an insoluble (heterogeneous) epoxidation catalyst which has high activity and selectivity and which may be readily recovered in active form from an epoxidation reaction mixture by filtration or similar separation techniques or which may be utilized in the form of a fixed bed or the like.

U.S. Pat. No. 4,367,342 discloses an olefin epoxidation process wherein an olefin is contacted with an organic hydroperoxide in the presence of an insoluble catalyst comprised of an inorganic oxygen compound of titanium. Such catalysts are further described in U.S. Pat. Nos. 4,021,454, 3,829,392 and 3,923,843. Unfortunately, catalysts of this type having consistently high activity and selectivity are recognized as being somewhat difficult to prepare, as relatively minor changes in the reactants or synthesis conditions employed result in significant variability in catalytic performance. Moreover, certain of the titanium reagents typically used for such purpose, such as titanium tetrachloride, are highly reactive and form corrosive by-products. Incorporation of relatively high levels of titanium into catalysts of this type, in an attempt to improve catalyst activity, has also been challenging. It is difficult to maintain uniform dispersion of the titanium throughout the catalyst (believed to be necessary for high selectivity to epoxide) as the amount of titanium is increased.

Consequently, it would be highly desirable to develop alternative methods of synthesizing heterogeneous titanium-containing catalysts which avoid the shortcomings of prior art procedures and reliably and conveniently provide materials having high activity and selectivity in olefin epoxidation reactions.

SUMMARY OF THE INVENTION

The invention provides a method of preparing a heterogeneous catalyst comprising combining a titanosiloxane polymer with a siliceous material selected from the group consisting of inorganic siliceous solids and siliceous sol gels to form a titanosiloxane polymer-containing catalyst precursor. The precursor is calcined to yield the heterogeneous catalyst.

DETAILED DESCRIPTION OF THE INVENTION

The titanosiloxane polymer utilized as a source of titanium in the process of the present invention may be any polymeric substance characterized by a backbone comprised of Si, Ti, and O atoms. The oxygen atoms are interspersed between adjoining Si atoms, Ti atoms, and Si and Ti atoms (e.g., —Si—O—Si—, —Ti—O—Ti— and —Si—O—Ti). Pendent to the Si and Ti atoms are organic groups, which preferably take the form of lower alkyl and/or alkoxide groups and/or aryl and/or aryloxide groups (e.g., —R and/or —OR wherein the R groups are the same or different and are selected from $C_1$–$C_6$ alkyl and $C_6$–$C_{10}$ aryl). The titanosiloxane polymer may be linear, branched, or cross-linked in structure. Such materials are well known in the art and are described, for example, in U.S. Pat. No. 3,873,578 and in the chapter entitled "Silicones" in the Encyclopedia of Polymer Science and Engineering, Vol. 15, pp. 230–232. Titanosiloxane polymers are also available commercially from sources such as Gelest, Inc. (Tullytown, Pa.).

Particularly preferred titanosiloxane polymers are those substances comprised of repeating units of

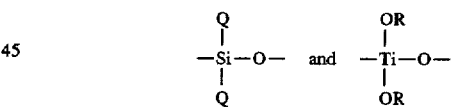

wherein the Q groups are the same or different and are selected from —OR and R and wherein the R groups are the same or different and are selected from the group consisting of $C_1$–$C_6$ alkyl groups (e.g., methyl, ethyl, n-propyl, isopropyl, n-butyl, iso-butyl, sec-butyl and the like) and $C_6$–$C_{10}$ aryl groups (e.g., phenyl, benzyl, tolyl, xylyl and the like). As mentioned previously, these materials may be linear or branched or cross-linked; the branching and cross-linking sites may be created by having individual Si or Ti atoms linked to more than two Si or Ti atoms through oxygen bonds.

Titanosiloxane polymers suitable for use in the present invention may be prepared by any known method. One such method (described in U.S. Pat. No. 3,873,578, incorporated herein by reference in its entirety) involves the hydrolysis in an alkaline medium of a silane and an ester of orthotitanic acid.

The molar ratio of Si to Ti in the titanosiloxane polymer is not critical and may be varied as desired to modify or optimize the properties of the final heterogeneous catalyst produced therefrom. Typically, however, the Si:Ti molar ratio is in the range of from about 15:1 to 1:1. In one desirable embodiment, the molar ratio is in the range of from about 10:1 to 5:1.

The titanosiloxane polymer is combined with a siliceous material selected from the group consisting of inorganic siliceous solids and siliceous sol gels to form a titanosiloxane polymer-containing catalyst precursor. The precise method by which the titanosiloxane polymer and the siliceous material are combined is not critical, but it will be desirable to employ a method whereby intimate association of these materials in the catalyst precursor is achieved. Where the siliceous material is an inorganic siliceous solid, for example, the titanosiloxane polymer is preferably introduced into the pores of the inorganic siliceous solid so that a substantial portion of the surface of the inorganic siliceous solid is coated with or brought into contact with the titanosiloxane polymer. In the case of a siliceous sol gel, intimate association can be accomplished by forming the sol gel in the presence of the titanosiloxane polymer in order that the two materials create, in effect, an interpenetrating network in the catalyst precursor.

The amount of titanosiloxane polymer utilized relative to the amount of siliceous material is not believed to be critical and may be readily varied in order to provide the level of titanium desired in the heterogeneous catalyst. For example, where a relatively high loading of titanium is sought, the weight ratio of titanosiloxane polymer:siliceous material may be increased. An alternative approach is to employ a lower weight ratio while decreasing the molar ratio of Si:Ti in the titanosiloxane polymer. Generally speaking, however, titanosiloxane polymer:siliceous material weight ratios in the range of from about 2:1 to 1:20 will be suitable for purposes of this invention.

Suitable inorganic siliceous solids for purpose of this invention are solid materials which contain a major proportion of silica (silicon dioxide). Amorphous (i.e., non-crystalline) silicon oxides are particularly preferred for use. In general, suitable inorganic siliceous solids are further characterized by having a relatively large surface area in relation to their mass. The term used herein and one normally used in the art to express the relationship of surface area to mass is "specific surface area". Numerically, specific surface area will be expressed as square meters per gram ($m^2/g$). Generally, the inorganic siliceous solid has a specific surface area of at least 1 $m^2/g$ and preferably the average specific surface area is from 25 $m^2/g$ to 800$^2$/g.

Suitable inorganic siliceous solids include synthetic porous silicas consisting of particles of amorphous silica flocculated or linked together so that they form relatively dense, close-packed masses. Representatives of such materials are silica gel and precipitated silica. These silica products are porous, in that they have numerous pores, voids, or interstices throughout their structures.

Other suitable inorganic siliceous solids include synthetic silica powders consisting of particles of amorphous silica flocculated in open-packed, readily disintegrated, loosely knit aggregates. Illustrative silica powders include fumed, pyrogenic silicas obtained by the combustion of hydrogen and oxygen with silicon tetrachloride or tetrafluoride.

Synthetic inorganic oxide materials containing a major proportion of silica comprise another class of inorganic siliceous solids. Such materials are known as refractory oxides and includes silica-alumina, silica-magnesia, silica-zirconia, silica-alumina-boric and silica-alumina-magnesia.

Particularly preferred synthetic inorganic siliceous solids are those consisting essentially of pure silica, e.g., materials containing at least 99% silica.

Siliceous inorganic solids are well-known in the art and have previously been used in the preparation of titanium-containing heterogeneous catalysts as described, for example, in U.S. Pat. Nos. 4,367,342, 4,021,454, 3,829,392 and 3,923,843, European Patent Publication Nos. 0129814, 0345856, 0492697 and 0734764, Japanese Kokai No. 77-07, 908 (Chem. Abstracts 98:135000s), PCT Application No. WO 94/23834, German Patent Document No. 3,205,648, and Castillo et al., *J. Catalysis* 161, pp. 524–529 (1996), the teachings of which are incorporated herein by reference in their entirety. Any of the siliceous inorganic solids described in these references are also suitable for use in the presently claimed invention.

A particularly preferred method of combining the titanosiloxane polymer with the siliceous inorganic solid is by impregnation. Any of the conventionally employed means of impregnating a porous solid with a liquid and/or soluble impregnating agent may be used. For example, the titanosiloxane polymer may be dissolved in a suitable solvent such as an alcohol and then admixed with the inorganic siliceous solid to form the catalyst precursor. "Incipient wetness" impregnation techniques, whereby a minimum quantity of solvent is utilized in order to avoid formation of a slurry, are also suitable for use. The resulting mixture may be aged, optionally with agitation or other mixing, prior to further processing. The solvent used for impregnation may thereafter be removed by drying at moderately elevated temperature (e.g., 50° C. to 200° C.) and/or reduced pressure (e.g., 1 mm Hg to 100 mm Hg) prior to calcination. The titanosiloxane polymer and the inorganic siliceous solids may alternatively be dry mixed to yield the precursor.

In another embodiment of the invention, the siliceous material combined with the titanosiloxane polymer is a siliceous sol gel. Suitable sol gels are gel materials comprised predominantly of silica (silicon dioxide). The formation of siliceous sol gels is well-known in the art and is generally accomplished by hydrolyzing siliceous-containing compounds and then condensing the hydrolyzed species resulting therefrom. It is believed that the sol gel process involves a three step reaction sequence wherein hydrolysis of a silicon alkoxide such as a tetraalkyl orthosilicate forms a hydroxylated product and the corresponding alcohol. This mechanism is highly dependent on pH and can be catalyzed under acidic, neutral or basic conditions. Next, condensation between an unhydrolyzed alkoxide group and a hydroxyl group or between two hydroxyl groups eliminates water or an alcohol and forms a colloidal mixture called a sol. In the third step, polycondensation between these colloidal sols and additional networking eventually results in a three dimensional network (the gel). These three steps may take place more or less simultaneously rather than sequentially. The catalyst used to promote the gelation or condensation reaction may be the same as or different than the catalyst used to accelerate the rate of hydrolysis. In one preferred embodiment of this invention, the hydrolysis reaction is catalyzed by a protic acid such as hydrochloric acid while the polycondensation reaction is catalyzed by the addition of a base such as ammonium hydroxide, a hydroxide salt of an ammonium species wherein nitrogen is substituted by from 1 to 4 organic groups such as $C_1-C_{10}$ alkyl, an alkali metal hydroxide such as sodium hydroxide or potassium hydroxide, or an alkaline earth metal hydroxide such as calcium hydroxide. In one embodiment, the precursor is obtained by treating a mixture of the titanosiloxane polymer and an acidic hydrozylate of a tetraalkyl orthosilicate with a base. The use of an alkali metal or alkaline earth metal compound as the base is particularly advantageous where it is desired to introduce an alkali metal or alkaline earth metal oxide or hydroxide into the final heterogeneous catalyst as a promoter. Typically, such promoters are incorporated at levels not in excess of 10% by weight (more preferably, from 0.01 to 5% by weight).

Suitable siliceous starting materials for use in the sol gel preparation may be any silicon-containing substance capable of being incorporated into the sol gel. Silicon alkoxides are most preferred, including, for example, tetrapropyl orthosilicate and other compounds meeting the formula $Si(OR)_4$ wherein the R groups are the same or different and are preferably selected from $C_1$ to $C_4$ alkyl. Alkoxides of metals other than silicon may also be utilized together with the silicon alkoxide, including, for example, titanium alkoxides, aluminum alkoxides, vanadium alkoxides, and alkoxides of other metals from Groups III A, IVA and VA of the Periodic Table. In a preferred embodiment of the invention, however, silicon alkoxide is the sole alkoxide present during formation of the sol gel.

While the exact point at which the titanosiloxane polymer is combined with the sol gel is not thought to be critical, it is typically preferred to introduce the titanosiloxane prior to the time when gelation is complete. In one embodiment, for example, acidic hydrolysis of the silicon alkoxide is initiated, followed by addition of the titanosiloxane polymer, and finally addition of a base to promote polycondensation in the presence of the titanosiloxane polymer. The exact mechanism by which the catalyst precursor is formed using the aforedescribed techniques is not known. It is possible that under the hydrolysis, condensation, and/or polycondensation reaction conditions some reaction between the silicon alkoxide (or its derivatives) and the titanosiloxane polymer takes place.

Water (or a source of water) must be added to the silicon alkoxide to achieve hydrolysis. The amount of water used to prepare the sol generally ranges from a mole ratio of water to total alkoxide in the solution of about 1:1 to about 20:1. Hydrolysis, may proceed in the presence or absence of solvent, but a solvent is generally employed if difficulties arise in obtaining a homogeneous solution of the silicon alkoxide and water. Generally, for economic reasons, the amount of solvent used is that which is the minimum effective amount. Suitable solvents include alcohols especially lower aliphatic alcohols such as isopropyl alcohol. Another role performed by the solvent is assisting in uniform and controlled hydrolysis and condensation of the silicon alkoxide by avoidance of excessively rapid reaction between the water and the silicon alkoxide.

Once the sol gel containing the titanosiloxane polymer has been formed, the catalyst precursor is preferably isolated by filtration, decantation, centrifugation or similar mechanical means from any free liquid which may be present and then, if so desired, washed with a suitable solvent such as water, a lower aliphatic alcohol or ketone or the like, and then dried under conditions analogous to those described previously for the preparation method starting with an inorganic siliceous solid.

The catalyst precursor is calcined by firing, preferably under an oxidizing atmosphere such as air or a nitrogen/oxygen mixture, at an elevated temperature. The preferred temperature range for calcination is in the range of from 500° C. to 900° C. Typically, calcination times of from about 0.5 to 24 hours will be sufficient to render the precursor active as a catalyst.

The heterogeneous catalyst thereby obtained will generally have a composition comprising from about 0.05 to 10 percent by weight titanium (in the form of titanium oxide, typically, and preferably, in a high positive oxidation state) with the balance being, in preferred embodiments of the invention, predominately or exclusively silica (silicon dioxide). The catalyst is typically porous in character, has a relatively high surface area, and may be characterized as comprising an inorganic oxygen compound of silicon in chemical combination with an inorganic oxygen compound of titanium (e.g., oxide or hydroxide).

Prior to use, the catalyst obtained by practice of this invention may be subjected to additional treatment or modification so as to optimize its catalytic properties for a particular application. One particularly desirable pretreatment method which may be utilized, for example, is to treat the catalyst with an organic silylating agent at elevated temperature. Such methods are well-known in the art and are described for example, in U.S. Pat. Nos. 3,829,392 and 3,923,843 (incorporated hereby by reference in their entirety). Suitable silylating agents include organosilanes, organosilylamines and organosilazanes.

Organosilanes containing from one to three organic substituents may be utilized, including, for example, chlorotrimethylsilane, dichlorodimethyl silane, nitrotrimethylsilane, chlorotriethylsilane, chlorodimethylphenylsilane and the like. Preferred organohalosilane silylating agents include tetrasubstituted silanes having from 1 to 3 halo substituents selected from chlorine, bromine, and iodine with the remainder of the substituents being methyl, ethyl or a combination thereof. Organodisilazanes are represented by the formula

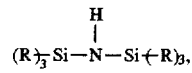

wherein the R groups are independently hydrocarbyl groups (preferably, $C_1$–$C_4$ alkyl) or hydrogen. Especially preferred for use are the hexaalkyl substituted disilazanes such as, for example, hexamethyldisilazane.

Treatment with the silylating agent may be performed either in the liquid phase (i.e., where the silylating agent is applied to the catalyst as a liquid, either by itself or as a solution in a suitable solvent such as a hydrocarbon) or in the vapor phase (i.e., where the silylating agent is contacted with the catalyst in the form of a gas). Treatment temperatures are preferably in the 100° C. to 450° C. range, with somewhat higher temperatures (e.g., 300° C. to 425° C.) being generally preferred wherein the silylating agent is an organohalosilane and somewhat lower temperatures (e.g., 100° C. to 300°) being preferred for the organosilazanes. The silylation may be carried out in a batch, semi-continuous, or continuous manner.

The length of time required for the silylating agent to react with the surface of the catalyst depends in part on the temperature and agent employed. Lower temperatures generally require longer reaction times. Generally, times of from 0.1 to 48 hours are suitable.

The amount of silylating agent employed can vary widely. Suitable amounts of silylating agent can range from about 1 percent by weight (based on the weight of the entire catalyst composition) to about 75 percent by weight, with amounts of from 2 to 50 percent by weight typically being preferred. The silylating agent can be applied to the catalyst either in one treatment or a series of treatments.

The catalyst may also be hydrated prior to silylation. Hydration is effected by contacting the catalyst with water and then heating it or by contacting the catalyst with steam at an elevated temperature (preferably, a temperature in excess of 100° C., more preferably, a temperature in the range of 150° C. to 450° C.) for from about 0.5 to 6 hours.

The heterogeneous catalyst compositions prepared by practice of the present invention can be utilized in oxidation reactions and are particularly useful for catalyzing the epoxidation of olefins (e.g., propylene) using organic hydroperoxides such as ethyl benzene hydroperoxide. Olefin epoxidations of this type are well-known in the art and are described, for example, in U.S. Pat. No. 4,367,342 (incorporated herein by reference in its entirety).

EXAMPLES

Example 1

This example illustrates the preparation of a titanium-containing catalyst in accordance with the invention wherein a sol gel containing a titanosiloxane polymer is formed as a catalyst precursor.

Tetraethylorthosilicate [Si(OEt)$_4$, 12.3 g] is dissolved in isopropyl alcohol to form a solution. Aqueous hydrochloric acid (0.1N HCl) is added to the solution, which is then stirred for 2 hours. A titanosiloxane polymer (2.0 g) described as a diethoxysiloxane-ethyl titanate copolymer obtained from a commercial source (Gelest, PSITI-019) is added to the acidic hydrozylate solution and the resulting mixture stirred for 15 minutes. Gel formation is accomplished by the addition of ammonium hydroxide. The resulting sol gel is washed with water until the filtrate is neutral and then washed once with acetone. The resulting product is air-dried, then dried in a vacuum oven. Calcination at 800° C. yields the titanium-containing catalyst (0.85 weight % Ti by elemental analysis).

Comparative Example 2

For comparative purposes, the procedure of Example 1 is repeated except that titanium isopropoxide [Ti($^i$OPr)$_4$] is used in place of the titanosiloxane polymer. The product thereby obtained contains 1.9 weight % titanium.

Example 3

This example illustrates the preparation of a titanium-containing catalyst in accordance with the invention wherein silica is impregnated with the titanosiloxane polymer. A 20 g quantity of silica (obtained from W. R. Grace as "Silica 432", having a particle size of 0.6–1.4 mm) was dried in air at 300° C. (ramp rate 10° C./min) for 6 hours. The dried silica and 100 mL isopropyl alcohol (obtained from Aldrich, anhydrous) were charged into a 2000 mL 3-neck round bottom flask equipped with stirrer and inert gas inlet. A solution containing 10 g isopropyl alcohol (Aldrich, anhydrous) and 10.0 g of the same titanosiloxane polymer used in Example 1 was then added dropwise to the contents of the flask over a 0.5 hour period. The resulting mixture was stirred 7 hours at room temperature under an inert gas atmosphere. The solids thus obtained were collected by filtration, washed with isopropyl alcohol, and then dried at ambient conditions in a hood overnight. The dried solids were then further dried in air at 150° C. for 1 hour and then calcined at 800° C. (5° C./min ramp) for 3 hours. The titanium-containing catalyst thus produced contained 0.6 weight percent Ti by elemental analysis.

Example 4

This example demonstrates the utility of titanium-containing catalysts prepared in accordance with the present invention in an olefin epoxidation reaction using an organic hydroperoxide. In each run, catalyst (0.5 g) was added to a 4-neck round bottom flask equipped with a condenser, thermocouple, stir bar and a sampling port. A mixture containing 17.9 g 1-octene, 10 g of an ethylbenzene hydroperoxide solution obtained by air oxidation of ethyl benzene, and 1 g nonane (internal standard) was added to the flask under an inert atmosphere. A sample was taken after the reaction mixture was stirred thoroughly. The mixture was then heated to 90° C. and maintained at that temperature for 1 hour. The observed performance of each catalyst is summarized in the following table.

| Catalyst | EBHP Conversion, % | Epoxide Selectivity, % |
|---|---|---|
| Example 1 | 85 | 74 |
| Comparative Example 2 | 81 | 64 |

An improvement in epoxide selectivity of approximately 10% was obtained at constant organic hydroperoxide conversion using a titanium-containing catalyst prepared using a titanosiloxane polymer in accordance with the invention as compared to a titanium-containing catalyst prepared using titanium isopropoxide as the source of titanium.

Example 5

The epoxidation procedure of Example 4 was repeated using the catalyst of Example 3 and a reaction temperature of 100° C. After 1 hour, ethylbenzene hydroperoxide conversion was 95% and epoxide selectivity was 76%.

Example 6

This example demonstrates that the titanium-containing catalysts prepared in accordance with the invention are heterogeneous in character and that their activity as epoxidation catalysts is not due to the presence of soluble titanium species.

A titanium-containing catalyst prepared in accordance with the invention (1 g) is placed in a round bottom flask. A mixture of 1-octene (34 g), ethyl benzene hydroperoxide solution (20 g), and nonane internal standard (2 g) is then added to the flask. The contents of the flask are heated to 90° C. using an oil bath. After 15 minutes at 90° C., half of the reaction solution is removed using a syringe equipped with a filter. The filtered liquid removed by syringe is then transferred to a second round-bottom flask placed in a 90° C. oil bath. The second flask is not charged with any catalyst. The reactions in both flasks are maintained at 90° C. for another 45 minutes.

The following table summarizes the results observed:

| Reaction Time, min. | EBHP Conversion, % (Flask 1) | EBHP Conversion, % (Flask 2) |
|---|---|---|
| 15 | 36 | 36 |
| 60 | 71 | 36 |
| last 45 minutes | 35 | 0 |

If catalytically active species were present in solution, the epoxidation reaction would continue in the absence of the solid titanium-containing catalyst charged to Flask 1. However, epoxidation occurs only in the presence of the solid titanium-containing catalyst; no further reaction occurs in Flask 2. This proves that the activity of the initially charged catalyst is not due to the formation or presence of solubilized (homogeneous) titanium compounds.

We claim:
1. A method of preparing a heterogeneous catalyst comprising:
    (a) combining (i) a titanosiloxane polymer obtained by hydrolysis in an alkaline medium of a silane and an ester of orthotitanic acid with a siliceous material selected from the group consisting of inorganic siliceous solids and siliceous sol gels to form a titanosiloxane polymer-containing catalyst precursor; and
    (b) calcining the titanosiloxane polymer-containing precursor to form the heterogeneous catalyst.
2. The method of claim 1 wherein the siliceous material is an inorganic siliceous solid and the inorganic siliceous solid is silica.
3. The method of claim 1 wherein the titanosiloxane polymer is comprised of repeating units of:

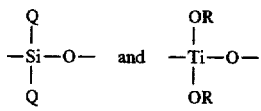

wherein the Q groups are the same or different and are selected from the group consisting of —R and —OR and wherein the R groups are the same or different and are selected from the group consisting of $C_1$–$C_6$ alkyl groups and $C_6$–$C_{10}$ aryl groups.
4. The method of claim 1 wherein the heterogeneous catalyst is comprised of from 0.5 to 5 weight percent titanium.
5. The method of claim 1 comprising the additional step of treating the heterogeneous catalyst with a silylating agent.
6. The method of claim 1 wherein the titanosiloxane polymer-containing catalyst precursor is obtained by impregnating an inorganic siliceous solid with the titanosiloxane polymer.
7. The method of claim 1 wherein the titanosiloxane polymer-containing catalyst precursor is obtained by treating a mixture of the titanosiloxane polymer and an acidic hydrozylate of a tetraalkyl orthosilicate with a base.
8. The method of claim 1 wherein the siliceous material is a siliceous sol gel obtained by treating an acidic hydrozylate of a tetraalkyl orthosilicate with a base.
9. A method of preparing a heterogeneous catalyst comprising:
    (a) impregnating silica having an average specific surface area of from 25 m²/g to 800 m²/g with a titanosiloxane polymer to form a titanosiloxane polymer-containing catalyst precursor; and
    (b) calcining the titanosiloxane polymer-containing catalyst precursor in the presence of oxygen to form the heterogeneous catalyst.
10. The method of claim 9 wherein step (a) is accomplished by application of a solution of the titanosiloxane polymer to the silica.
11. The method of claim 9 wherein the Q groups are $C_1$–$C_6$ alkoxy groups.
12. A method of preparing a heterogeneous catalyst comprising:
    (a) treating a mixture comprised of a titanosiloxane polymer and an acidic hydrozylate of a tetraalkyl orthosilicate with a base to form a titanosiloxane polymer-containing catalyst precursor; and
    (b) calcining the titanosiloxane polymer-containing catalyst precursor in the presence of oxygen to form the heterogeneous catalyst;

wherein the titanosiloxane polymer is comprised of repeating units of

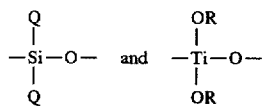

wherein the Q groups are the same of different and are selected from the group consisting of —R and —OR and wherein the R groups are the same or different and are selected from the group consisting of $C_1$–$C_6$ alkyl groups and $C_6$–$C_{10}$ aryl groups.
13. The method of claim 12 wherein the base corresponds to $R^1_4$NOH with the $R^1$ groups being the same or different and selected from the group consisting of hydrogen and $C_1$–$C_{10}$ alkyl.
14. A method of preparing a heterogeneous catalyst comprising:
    (a) combining a titanosiloxane polymer with a siliceous material selected from the group consisting of inorganic siliceous solids and siliceous sol gels to form a titanosiloxane polymer-containing catalyst precursor;
    (b) calcining the titanosiloxane polymer-containing precursor to form the heterogeneous catalyst; and
    (c) treating the heterogeneous catalyst with a silylating agent.
15. The method of claim 14 wherein the siliceous material is an inorganic siliceous solid and the inorganic siliceous solid is silica.
16. The method of claim 14 wherein the titanosiloxane polymer is comprised of repeating units of:

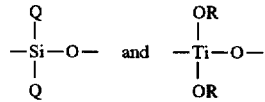

wherein the Q groups are the same or different and are selected from the group consisting of —R and —OR and wherein the R groups are the same or different and are selected from the group consisting of $C_1$–$C_6$ alkyl groups and $C_6$–$C_{10}$ aryl groups.
17. The method of claim 14 wherein the titanosiloxane polymer-containing catalyst precursor is obtained by impregnating an inorganic siliceous solid with the titanosiloxane polymer.
18. The method of claim 14 wherein the heterogeneous catalyst is comprised of from 0.5 to 5 weight percent titanium.
19. A method of preparing a heterogeneous catalyst comprising:
    (a) forming a titanosiloxane polymer-containing catalyst precursor by impregnating an inorganic siliceous solid with a titanosiloxane polymer; and
    (b) calcining the titanosiloxane polymer-containing precursor to form the heterogeneous catalyst.
20. The method of claim 19 wherein the inorganic siliceous solid is silica.
21. The method of claim 19 wherein the titanosiloxane polymer is comprised of repeating units of:

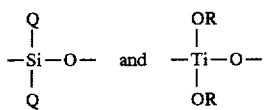

wherein the Q groups are the same or different and are selected from the group consisting of —R and —OR and wherein the R groups are the same or different and are selected from the group consisting of $C_1$–$C_6$ alkyl groups and $C_6$–$C_{10}$ aryl groups.

22. The method of claim 19 wherein the titanosiloxane polymer is obtained by hydrolysis in an alkaline medium of a silane and an ester of orthotitanic acid.

23. The method of claim 19 wherein the heterogeneous catalyst is comprised of from 0.5 to 5 weight percent titanium.

24. A method of preparing a heterogeneous catalyst comprising:
(a) forming a titanosiloxane polymer-containing catalyst precursor by treating a mixture of a titanosiloxane polymer and an acidic hydrozylate of a tetraalkyl orthosilicate with a base; and
(b) calcining the titanosiloxane polymer-containing precursor to form the heterogeneous catalyst.

25. The method of claim 24 wherein the titanosiloxane polymer is comprised of repeating units of:

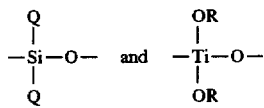

wherein the Q groups are the same or different and are selected from the group consisting of —R and —OR and wherein the R groups are the same or different and are selected from the group consisting of $C_1$–$C_6$ alkyl groups and $C_6$–$C_{10}$ aryl groups.

26. The method of claim 24 wherein the titanosiloxane polymer is obtained by hydrolysis in an alkaline medium of a silane and an ester of orthotitanic acid.

27. The method of claim 24 wherein the heterogeneous catalyst is comprised of from 0.5 to 5 weight percent titanium.

28. A method of preparing a heterogeneous catalyst comprising:
(a) combining a titanosiloxane polymer with a siliceous sol gel obtained by treating an acidic hydrozylate of a tetraalkyl orthosilicate with a base to form a titanosiloxane polymer-containing catalyst precursor; and
(b) calcining the titanosiloxane polymer-containing precursor to form the heterogeneous catalyst.

29. The method of claim 28 wherein the titanosiloxane polymer is comprised of repeating units of:

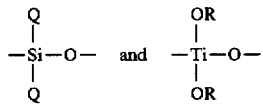

wherein the Q groups are the same or different and are selected from the group consisting of —R and —OR and wherein the R groups are the same or different and are selected from the group consisting of $C_1$–$C_6$ alkyl groups and $C_6$–$C_{10}$ aryl groups.

30. The method of claim 28 wherein the titanosiloxane polymer is obtained by hydrolysis in an alkaline medium of a silane and an ester of orthotitanic acid.

31. The method of claim 28 wherein the heterogeneous catalyst is comprised of from 0.5 to 5 weight percent titanium.

32. The method of claim 9 wherein the titanosiloxane polymer is comprised of repeating units of

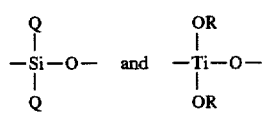

wherein the Q groups are the same or different and are selected from the group consisting of —R and —OR and wherein the R groups are the same or different and are selected from the group consisting of $C_1$–$C_6$ alkyl groups and $C_6$–$C_{10}$ aryl groups.

33. The method of claim 9 wherein the titanosiloxane polymer is obtained by hydrolysis in an alkaline medium of a silane and an ester of orthotitanic acid.

34. The method of claim 9 wherein the heterogeneous catalyst is comprised of from 0.5 to 5 weight percent titanium.

* * * * *